United States Patent
Svensson et al.

(10) Patent No.: US 11,636,594 B2
(45) Date of Patent: Apr. 25, 2023

(54) SYSTEM AND METHOD FOR PROVIDING AN EXTENDED IMAGE OF A PATIENT

(71) Applicant: RaySearch Laboratories AB, Stockholm (SE)

(72) Inventors: Stina Svensson, Stockholm (SE); Sebastian Andersson, Stockholm (SE); Kjell Eriksson, Balsta (SE); Ola Weistrand, Huddinge (SE)

(73) Assignee: Raysearch Laboratories AB (Publ), Stockholm (SE)

( * ) Notice: Subject to any disclaimer, the term of this patent is extended or adjusted under 35 U.S.C. 154(b) by 0 days.

(21) Appl. No.: 17/596,270

(22) PCT Filed: Jun. 1, 2020

(86) PCT No.: PCT/EP2020/065109
§ 371 (c)(1),
(2) Date: Dec. 7, 2021

(87) PCT Pub. No.: WO2020/249413
PCT Pub. Date: Dec. 17, 2020

(65) Prior Publication Data
US 2022/0207727 A1    Jun. 30, 2022

(30) Foreign Application Priority Data
Jun. 13, 2019  (EP) ................................ 19180019

(51) Int. Cl.
*G06T 7/00* (2017.01)
*G06T 7/70* (2017.01)
(Continued)

(52) U.S. Cl.
CPC .......... *G06T 7/0012* (2013.01); *A61N 5/1031* (2013.01); *A61N 5/1049* (2013.01);
(Continued)

(58) Field of Classification Search
CPC ......... G06T 7/0012; G06T 7/70; G06V 10/44; G06V 10/755; A61N 5/1031;
(Continued)

(56) References Cited

U.S. PATENT DOCUMENTS

2015/0087880 A1* 3/2015 Velazquez Miranda ..................... A61K 31/80 600/1
2017/0178391 A1* 6/2017 Svensson ................ G16Z 99/00
(Continued)

FOREIGN PATENT DOCUMENTS

DE  2014216718 A1  2/2016
EP     3181049 B1  2/2018
(Continued)

OTHER PUBLICATIONS

International Search Report. International application No. PCT/EP2020/065109. Patent Cooperation Treaty. European Patent Office, P.B. 5818 Patentlaan 2, NL—2280 HV Rijswijk. Dated Sep. 17, 2020. pp. 1-4.
(Continued)

*Primary Examiner* — Vu Le
*Assistant Examiner* — Winta Gebreslassie
(74) *Attorney, Agent, or Firm* — Noréns Patentbyrå AB; Fredrik Mollborn

(57) ABSTRACT

A computer based method of obtaining a 3D image of a part of a patient's body is disclosed, based on a fraction image having a limited field-of-view and extending the field of view with information from an image of the patient's outline, obtained from a surface scan of the patient. Anatomical data from the planning image are preferably used to fill in the outline image, by means of a contour-guided deformable registration between the planning image and contour.

9 Claims, 3 Drawing Sheets

(51) Int. Cl.
  *G06V 10/44* (2022.01)
  *G06V 10/75* (2022.01)
  *A61N 5/10* (2006.01)

(52) U.S. Cl.
  CPC ............... *G06T 7/70* (2017.01); *G06V 10/44* (2022.01); *G06V 10/755* (2022.01); *A61N 2005/1061* (2013.01); *G06T 2207/10081* (2013.01); *G06T 2207/30008* (2013.01)

(58) Field of Classification Search
  CPC .......... A61N 5/1049; A61N 2005/1061; A61N 2005/10081; A61N 2005/30008
  See application file for complete search history.

(56) References Cited

U.S. PATENT DOCUMENTS

| 2017/0224298 | A1* | 8/2017 | Hannemann | A61B 6/469 |
| 2019/0066260 | A1 | 2/2019 | Suehling et al. | |
| 2019/0220986 | A1* | 7/2019 | Magro | A61B 6/032 |
| 2020/0349726 | A1* | 11/2020 | Magro | G06T 7/30 |

FOREIGN PATENT DOCUMENTS

| EP | 3378534 | A1 | 9/2018 |
| EP | 3449830 | A1 | 3/2019 |
| JP | 2013223792 | A | 10/2013 |
| JP | 2017093516 | A | 6/2017 |
| JP | 2017109099 | A | 6/2017 |
| JP | 2017217137 | A | 12/2017 |
| JP | 2019010508 | A | 1/2019 |

OTHER PUBLICATIONS

Ruchala, Olivera, Kapatoes, Reckwerdt and Mackie: Methods for improving limited field-of-view radiotherapy reconstruction using imperfect a priori images, Medical Physics 29, 2590 (2002).
Weistrand Ola et al: "The Anaconda algorithm for deformable image registration in radiotherapy", A Medical Physics, AIP, Melville, NY, US, vol. 42, No. I, Dec. 16, 2014 (Dec. 16, 2014), pp. 40-53.
Written Opinion of the International Searching Authority. International application No. PCT/EP2020/065109. Filing date: Jan. 6, 2020. Patent Cooperation Treaty. European Patent Office, D-80298 Munich. Dated Sep. 17, 2020. pp. 1-5.
Office Action dated May 11, 2022 in corresponding Japanese patent application No. 2021-573347, including English translation.

* cited by examiner

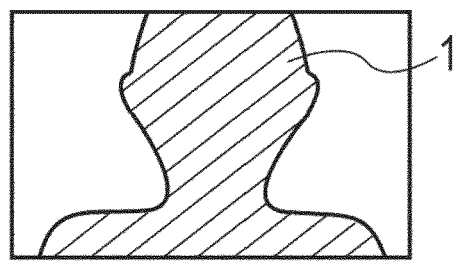
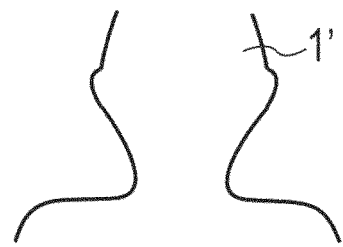
FIGURE 1a     FIGURE 1b
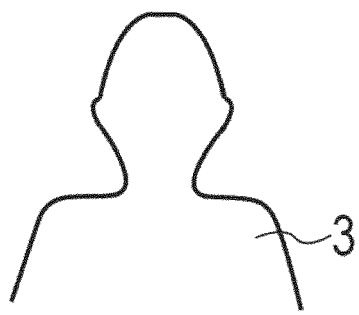
FIGURE 1c
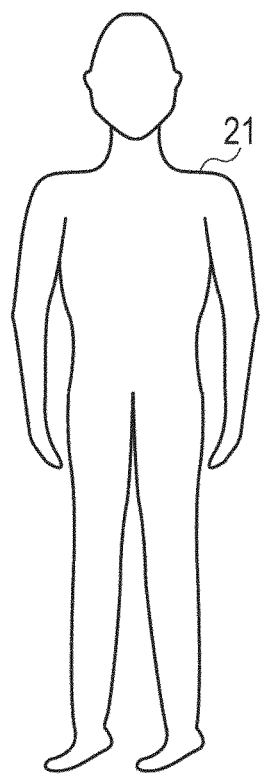 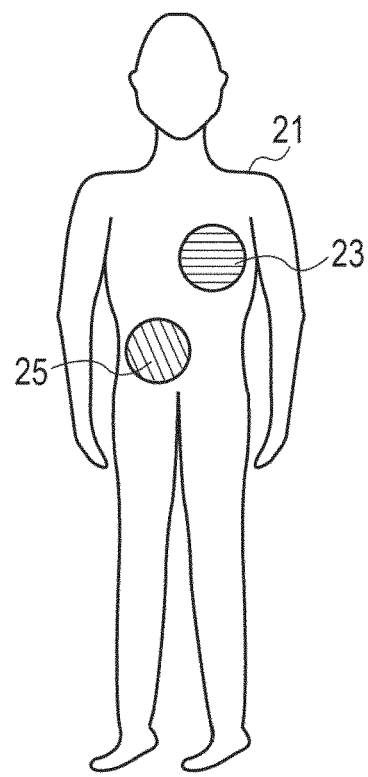 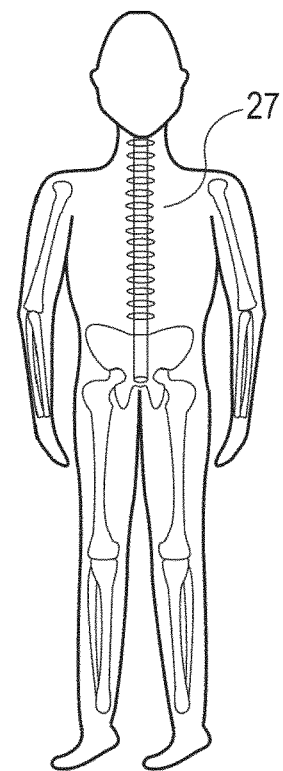
FIGURE 2a     FIGURE 2b     FIGURE 2c

SYSTEM AND METHOD FOR PROVIDING AN EXTENDED IMAGE OF A PATIENT

TECHNICAL FIELD

The present invention relates to a method, a computer program product and a computer system for providing an image of a patient, which may be used for example in radiotherapy treatment planning.

BACKGROUND

Radiotherapy treatment is generally distributed to a patient in a number of sessions, or fractions. Before the treatment starts, a planning image of the patient is obtained. The planning image provides input data to a treatment plan, which defines the treatment to be given to the patient, in terms of treatment modality, dose, beam angles and other variables. Before each session a fraction image is obtained, to assist in positioning the patient with respect to the treatment unit before the delivery. The fraction images can also be used to assess the dose actually delivered to the patient during the session and to study changes in patient-geometry that have occurred since the planning image was acquired. Such changes are important for treatment evaluation and the result of the evaluation may lead to a decision that modifications of the treatment plan are required. In the context of this description, both the planning image and the fraction images are typically 3D images constructed from a number of 2D images constituting projections of the patient's body.

Dose planning requires information about the location of the various organs and also about their material properties, such as density and/or atomic composition. Density information is used for dose planning. If photon radiotherapy is used, the density and atomic composition determine the attenuation of the radiation. If ion radiotherapy such as proton radiotherapy is used, the density and atomic composition determine the stopping power, which affects the distance that the ions will travel within the patient's body. For the initial planning, this information is taken from the planning image. The fraction images are typically used to determine the new boundaries of the regions of interest in order to aim the radiation beams correctly.

Therefore, the planning image should comprise information not only about the contours but also about the material properties of each region of interest. As the geometry of the tumor and other tissues changes during the course of therapy, the fraction images are used to obtain up-to-date contour information. However, the fraction images may have considerably less information than the planning images, in particular regarding material properties. For example, a fan beam CT scan (referred to in this document as CT) may be used for the planning image while Cone Beam CT (CBCT) scans are used for the fraction images. CT images comprise all the information needed for dose planning but are relatively expensive and CT imaging devices are more difficult to incorporate in a gantry than a CBCT imaging device. CBCT on the other hand, typically give images with a more restricted field of view than CT images.

Typically, the field-of-view for a CBCT image does not cover the full patient outline. This means that when computing dose based on a CBCT image, for example a fraction image the densities for the parts outside of the field-of-view of the CBCT image need to be estimated for dose computation. One solution would be to superimpose the patient's outline from the planning image onto the fraction image and assuming that it has the same properties as water. Water is a reasonable compromise, as it is a good approximation for most parts of the body, but this solution still causes inaccuracies in the dose computation.

Ruchala, Olivera, Kapatoes, Reckwerdt and Mackie: Methods for improving limited field-of-view radiotherapy reconstruction using imperfect a priori images, Medical Physics 29, 2590 (2002); doi: 10.1118/1.1513163, discloses a method of handling this problem working directly in the 2D images which are afterwards used to construct the 3D image. The method proposed by Ruchala et al. is not applicable when working directly with 3D images. Typically, the treatment planning system does not provide access to the 2D images so any changes made through these systems must be made in the 3D image.

European Patent publication EP3181049 proposes to use data from the planning image outside the field of view of the fraction image, to create a model outline of a part of the patient's body and include material information from the planning image outside the field of view of the fraction image to obtain a composite image having information from the fraction image where available and information from the planning image outside of this area. Planning images are not always available or the patient may have changed so much, for example due to weight loss that the planning image has become less relevant.

SUMMARY

It is an object of the present invention to provide an extended image of a patient including based on a first image having a limited field of view, the extended image having a greater field of view.

This object is achieved according to the present invention by a computer-based method of creating a composite image of a patient, comprising the steps of
a. providing a first image of a portion of a person, said first image having a first field of view
b. providing a surface scan corresponding to the exterior of the person
c. providing a second image of the outer contour of at least a part of the person based on the surface scan, said outer contour comprising an area of the patient corresponding to the first field of view and extending outside of the first field of view.
d. providing approximate image data inside of the outer contour, to produce an approximate image of the interior of the person
e. applying data from the first image in the area of the approximate image corresponding to the first field of view to create a composite image.

In this way, a composite image is obtained, comprising up-to-date information from the fraction image in the areas where such information is available, and anatomical information based on a surface scan and adapted to the fraction image, in areas outside the second field-of-view. Thus, the composite image comprises image data from the first image where such image data is available and approximate data in a second portion outside of the first portion. The first image is often referred to in this document as the fraction image and is typically but not necessarily a CBCT image. It should be understood that it may be any image where there is a desire to expand the field of view of the image.

The surface scan is used to generate an outer contour of the whole patient or part of the patient, filled with an approximation of the patient's anatomy.

The use of surface scanning apparatus is becoming more widely spread in radiotherapy treatment units, where they are used for ensuring correct positioning of patients for delivery of treatment fractions. According to the invention, such apparatus can be used for the purpose of providing approximate images of the patient that can be used to expand the field of view of another image of the patient, for example a CT or a CBCT image. Providing full body images, including an approximation of the body outside of the field of view is useful, for example in dose planning as discussed in the background section. A full body image can also be used for other purposes, such as positioning the patient, for example for radiotherapy, both to ensure correct treatment and to ensure that the patient will not be in the way as the couch and/or gantry move. Such images may also be useful for other applications, for example for planning medical procedures such as surgery.

Approximate image data for the interior of the contour may be estimated in a number of ways, depending on the types of information and level of detail and accuracy needed for a particular purpose. For example, the density value in the entire interior may be set to an appropriate density value, such as the density of water. It is also possible to combine the single density value with data about the position and extent of the bone structure within the patient, obtained, for example, from X-ray imaging, such as fluoroscopy.

In some embodiments, the step of providing approximate image data inside of the outer contour comprises including anatomical image data from an image such as a CT image. The CT image may be an earlier image of the same patient, or an atlas image that is representative in view of the patient's characteristics. The image data from the CT image is fit into the contour by means of a deformable registration of the CT image to the outer contour and setting the approximate image data based on the result of the deformable registration.

If bone structure data are available, the CT image may be deformably registered to both the outer contour and to the data regarding position and density of bone within the patient The invention also relates to a computer program product, preferably on a carrier, such as a non-transitory storage medium, for controlling a computer, said computer program product comprising computer-readable code arranged to cause the computer to perform the method according to any one of the preceding claims.

The method is primarily intended for use in connection with a radiotherapy apparatus although it may find other uses as discussed briefly above. The invention therefore also relates to a computer system comprising a processor, a data memory and a program memory. The data memory is arranged to hold at least one set of surface data, or contour information, and/or at least one fraction image and the program memory is arranged to hold a computer program product as defined above, in such a way that the computer program product can be used to control the processor. As will be understood, the inventive method itself can be performed in any computer having the necessary software installed.

The approximate image and the fraction image preferably comprise the same type of data. This means that if the fraction image is a CT or CBCT image, the same type of data should be used inside the contour. If the fraction image is an MRI image, the data provided inside the contour should be MRI image. It is also possible to create a synthetic CT image from an MRI image, that is, an image comprising the same types of data as a CT image. Such a synthetic CT image could be used as a planning or fraction image, together with other CT or CBCT images as fraction images.

Obtaining the anatomical data for the approximate image from a high-quality CT scan, such as a planning image, is particularly advantageous, since it provides high-quality approximate data without the need for a complete CT scan each time. This saves time and resources and also avoids unnecessary dose to the patient.

BRIEF DESCRIPTION OF THE DRAWINGS

The invention will be described in more detail in the following, by way of example and with reference to the appended drawings, in which FIGS. 1a and 1b show a 3D image of the head and neck of a patient and FIG. 1c shows a completed contour of the same area.

FIGS. 2a, 2b and 2c illustrate a contour obtained from a surface scan of the patient with approximated anatomical information inside.

DETAILED DESCRIPTION

Figure 3A:
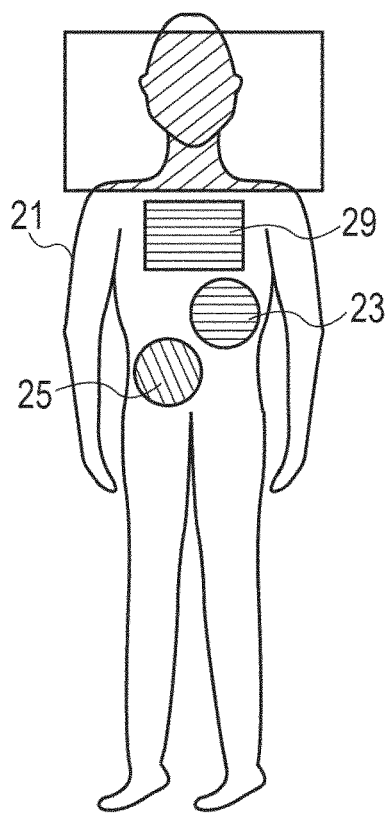
FIGS. 3a and 3b show examples of composite images in which 3D patient image with values inside limited field of view taken from the 3D image and values outside the limited field of view based on a surface scan of the patient.

FIG. 1a shows a coronal slice of a 3D image, comprising anatomical data about a patient but having a limited field-of-view which in at least some directions does not include the patient's outer contour. In particular, in this example, the top of the patient's head and an area from the shoulders down are not included. FIG. 1b shows the patient outline from the 3D image. The method according to the invention is applicable to any type of anatomical image but may be particularly useful for fraction images used in radiotherapy treatment planning Therefore, in this description, the term fraction image is often used, with the understanding that the invention may be used to extend any patient image having a limited field of view. The patient outline is obtained with known methods and will be referred to in this document as the fraction outline.

The aim is to obtain an image having all the data from the fraction image but a greater field-of-view than the limited field-of-view. In the area outside of the limited field-of-view, contour data taken from a surface scan of the patient, and possibly approximated anatomical data, are used to complement the fraction image. FIG. 1c illustrates such a contour of the head and neck area of the patient, which may be used to complement the image of FIG. 1a. The resulting fraction image, complemented with an approximate outline of parts of the patient's body that are outside of the limited field of view of the fraction image, is referred to in this document as an enhanced fraction image. An enhanced fraction image, in which contour information an approximate anatomical data has been added outside of the field-of-view of the fraction image based on information from the surface scan, is referred to as a composite image.

FIGS. 2a, 2b and and 2c show, schematically, a first, a second and a third simplified approximate image of a patient, based on an outline 21 of the patient obtained by surface scanning. In FIG. 2a, it is assumed that the density of the patient is homogeneous, so the approximate image is created by setting the density inside the contour to a suitable density, for example, that of water. FIG. 2b includes a more detailed approximation of the interior of the patient, indicated by the presence of a first 23 and a second organ 25 inside the patient, that may correspond, for example, to the liver and the heart. FIG. 2c illustrates another embodiment in which image data concerning the patient's bone structure, shown somewhat simplified, has been included. Such data may be obtained, for example, by a suitable X-ray method. The rest of the interior is in this example assumed to have the density of water. Preferably, the interior of the patient in the approximate image is a realistic image of the patient, based on an image which may be an earlier image of the patient or on an atlas image. Co-pending application (EP19180004.4) discusses in detail how the interior of the patient may be approximated on various level of accuracy to produce an approximate image based on the surface scan.

In a preferred embodiment, the approximate image is based on patient outline data obtained from the surface scan and interior data about the anatomy, obtained from a planning image taken at an earlier time. Such an approximate image, with the level of detail and accuracy selected based on the requirements of the situation, may be used, together with the fraction image, to obtain a composite image. The surface scan is preferably taken at the later time, to provide as accurate contour data as possible. In this embodiment, the current anatomical data inside the contour are approximated by a deformable registration between the planning image and the outline data, and the approximate anatomical data inside the contour are set based on the result of the deformation of the planning image. In addition to this, information obtained from X-ray imaging, such as fluoroscopy, obtained at the same time as the surface scan, can also be added into the contour of the patient. The information about bone structures obtained from X-ray images can be used to improve the deformable registration of the planning image to the contour to improve the image outside the fraction image field of view. FIG. 2c shows, schematically, a simplified approximate image including the bone structure of the patient.

The planning image normally has a larger field of view than the fraction image but does not always cover the whole portion of patient that should be imaged. In many cases, the planning image may be used to extend the fraction image using the planning image as discussed in European Patent publication EP3181049 and use the contour data outside of the field of view of the planning image. In this case, therefore, the approximate image may comprise data from the deformed planning image in the field of view of the planning image and approximate data obtained in another way in the rest of the contour, for example obtained as discussed for FIG. 2a, 2b or 2c.

FIG. 3a shows a composite image in which the image shown in FIG. 1a has been combined with the outline 21 shown in FIG. 2b to create a composite image with accurate date in the head and neck region and approximate data for the rest of the body.

Figure 3B:
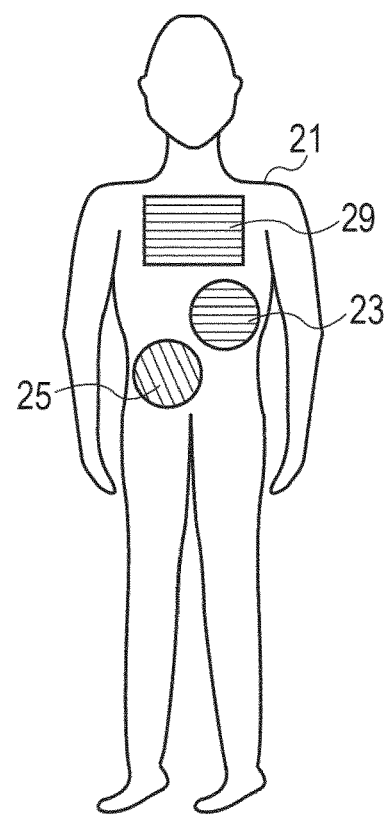

FIG. 3b shows a composite image where the data in the field of view of the fraction image 29 is taken from the fraction image and the data outside the field of view is taken from the approximate image 21 based on the surface scan and interior data obtained, for example, from the planning image, as discussed above. In this example, as is sometimes the case, the fraction image does not include any portion of the patient's contour. As discussed above, the approximate image preferably also includes anatomical data obtained from an image, such as a planning image of the patient. Of course, the data taken from the fraction image may include only data from a limited part of the fraction image, for example, if some parts of the image are known to have a low quality.

Figure 4:
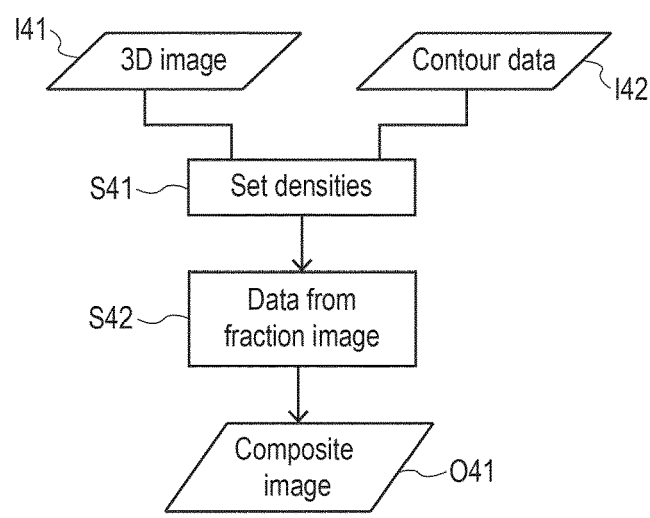
FIG. 4 is a flow chart of a method according to the invention.

FIG. 4 is a flow chart of a method according to the invention. Input data are a 3D image (I41) with limited field of view, typically a CBCT image for use as a fraction image, and contour data (I42) covering the whole patient, or at least a larger portion of the patient than the limited field of view of the 3D image and including at least a portion of the patient's outer contour based on a surface scan. An example of how to calculate the contour data based on the surface scan is given in (EP19180004.4).

In a first step S41, appropriate densities are set inside the interior of the contour. As discussed above in connection with FIGS. 2a-2c, this may be done on a suitable level of detail of accuracy depending on what is required by the situation. In a preferred embodiment the densities are set based on a deformation of a high-quality CT image taken at an earlier stage, such as a planning image. The densities may also be taken from an atlas image representing a similar patient. In that case, the CT image, or atlas image, is registered to the outer contour to obtain anatomical data that may be applied inside of the outer contour.

In a second step S42, data from the fraction image are included in the approximate image. This may be done by setting the data values in the portion of the approximate image corresponding to the field of view that should be included from the fraction image to 0 and then inserting the data values from the fraction image in that portion. Typically, data from the whole fraction image are used, so that the composite image will have data from the fraction image in the whole field of view of the fraction image. As will be understood, however, data from only a part of the fraction image may be included. The output from the procedure is a composite image O41 comprising data from the fraction image where available and providing a larger field of view by means of an approximate image based on the surface contour of all or a part of the patient. Typically, the surface scan on which the approximate image is based, and the fraction image are taken at approximately the same time, in which case the images can be combined without the need for registration. In other cases, a rigid or deformable registration may be useful to adapt the images to each other.

Before adapting the model outline to the fraction image, an initial overlap between the contour and the fraction image is preferably determined. This may be achieved by using an automatic rigid registration algorithm between the contour and the fraction image. The images may also be superimposed based on a visual assessment of the initial overlap, or in any other suitable way.

Instead of using contour data related to the same patient as the 3D image, it may in some cases be sufficient to provide contour data that is similar in size and shape to the patient but obtained from another source, such as an atlas.

Figure 5:
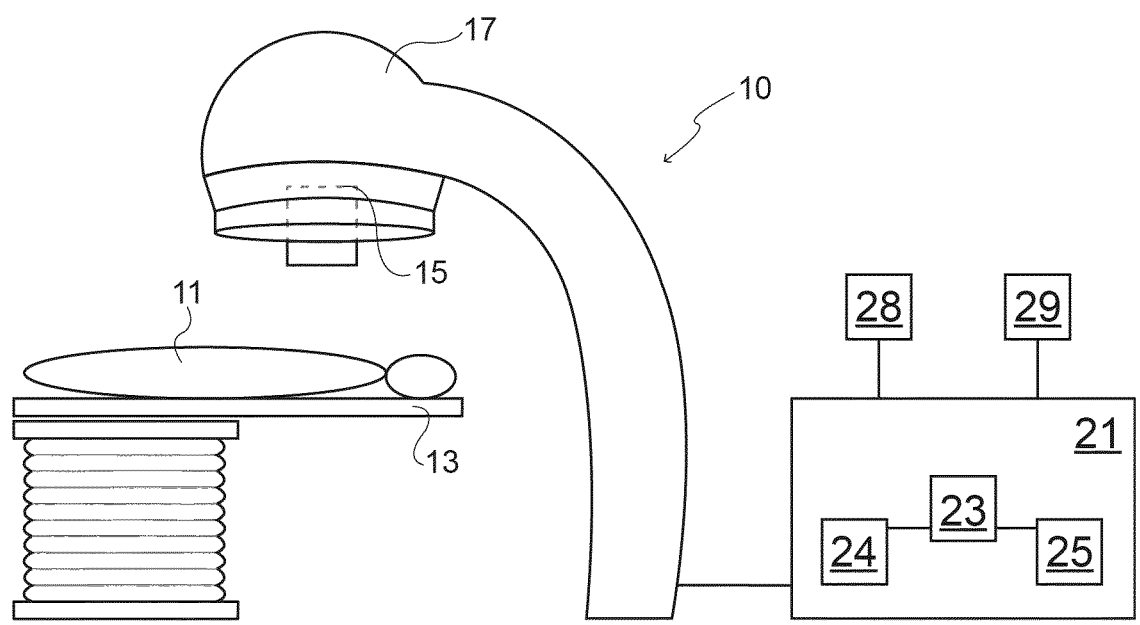
FIG. 5 is a schematic drawing of a system that may be used to perform the invention.

FIG. 5 is an overview of a system 10 for radiotherapy treatment and/or treatment planning. As will be understood, such systems may be designed in any suitable way and the design shown in FIG. 5 is only an example. A patient 11 is positioned on a treatment couch 13. The system comprises an imaging/treatment unit having a radiation source 15 mounted in a gantry 17 for emitting radiation towards the patient positioned on the couch 13. Typically, the couch 13 and the gantry 17 are movable in several dimensions relative to each other, to provide radiation to the patient as flexibly and correctly as possible. These parts and their functions are well known to the skilled person. A number of passive devices provided to shape the beam laterally and in depth are typically present and will not be discussed in more detail here. In this example the system also comprises an optical scanner for providing data related to the outer contour of the patient and enabling the generation of a contour image of the whole or part of the patient's body. The system also comprises a computer 21 which may be used for radiotherapy treatment planning and/or for controlling radiotherapy treatment. As will be understood, the computer 21 may be a separate unit not connected to the imaging/treatment unit.

The computer 21 comprises a processor 23, a data memory 24, and a program memory 25. Preferably, one or more user input means 28, 29 are also present, in the form of a keyboard, a mouse, a joystick, voice recognition means or any other available user input means. The user input means may also be arranged to receive data from an external memory unit.

The data memory 24 comprises clinical data and/or other information used to obtain a treatment plan, including the contour data provided by the contour scanner. The data memory 24 also comprises one or more patient images to be used in treatment planning according to embodiments of the invention. The nature of these patient images, and how they may be obtained, has been discussed above. The program memory 25 holds at least one computer program arranged to cause the processor to perform a method according to FIG. 4. The program memory 25 also holds a computer program arranged to make the computer perform the method steps discussed in connection with FIG. 4 and/or a computer program arranged to make the computer control the radiotherapy treatment of a patient.

As will be understood, the data memory 24 and the program memory 25 are shown and discussed only schematically. There may be several data memory units, each holding one or more different types of data, or one data memory holding all data in a suitably structured way, and the same holds for the program memories. One or more memories may also be stored on other computers. For example, the computer may be arranged to perform only one of the methods, there being another computer for performing the optimization.

The invention claimed is:

1. A computer-implemented method of creating a composite image of a patient, comprising the steps of:
    a. acquiring a first 3D image of a portion of a person, said first image having a first field of view;
    b. acquiring a surface scan corresponding to the exterior of the person;
    c. acquiring a second 3D image of the outer contour of at least a part of the person based on the surface scan, said outer contour comprising an area of the patient corresponding to the first field of view and extending outside of the first field of view;
    d. acquiring approximate image data inside of the outer contour, to produce an approximate 3D image of the interior of the person, wherein acquiring approximate image data includes setting a suitable uniform density value inside at least a part of the outer contour, the uniform density value being a predetermined density value, or being based on a CT image; and
    e. applying data from the first image in the area of the approximate image corresponding to the first field of view to create a composite 3D image.

2. A method according to claim 1, wherein the first image is a CBCT image.

3. A method according to claim 1, wherein the step of acquiring approximate image data inside of the outer contour comprises including data regarding the position and density of bone within the patient, inside of the contour.

4. A method according to claim 1, wherein the step of acquiring approximate image data inside of the outer contour comprises deformable registration of the CT image of the person to the outer contour and setting the approximate image data based on the result of the deformable registration.

5. A method according to claim 4, wherein:
    the step of acquiring approximate image data inside of the outer contour comprises including data regarding the position and density of bone within the patient, inside of the contour, and
    the CT image is deformably registered to the outer contour and to the data regarding position and density of bone within the patient.

6. A method according to claim 1, wherein the step of acquiring approximate image data inside of the outer contour comprises deformable registration of an atlas image to the outer contour and setting the approximate image data based on the result of the deformable registration.

7. A computer program product, stored in a non-transitory storage medium which, when run in a computer causes the computer to perform the method of claim 1.

8. A computer system for providing an approximate image of a patient, the system comprising processing means and a program memory having stored therein instructions that when executed by the processing means, causes the computer system to perform the method of claim 1.

9. A computer system according to claim 8, further comprising a contour scanning device arranged to provide contour data representing the contour or the patient's body and wherein the processor is arranged to calculate the model of the contour based on the contour data.

* * * * *